(12) United States Patent
Badorc et al.

(10) Patent No.: US 8,034,828 B2
(45) Date of Patent: *Oct. 11, 2011

(54) USE OF FGF INHIBITING SUBSTITUTED 1,2,3 INDOLIZINE DERIVATIVES IN THE PREPARATION OF MEDICAMENTS WHICH CAN BE USED TO TREAT DISEASES LINKED TO PATHOLOGICAL CHOROIDAL ANGIOGENESIS

(75) Inventors: Alain Badorc, Roquettes (FR); Francoise Bono, Toulouse (FR); Marie-Francoise Bordes, Labarthe sur Leze (FR); Jean-Michel Foidart, Trooz (BE); Nathalie Guillo, Toulouse (FR); Agnes Noel, Durbuy (BE); Jean-Marie Rakic, Flostoy (BE)

(73) Assignee: Sanofi-Aventis, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/201,075

(22) Filed: Aug. 29, 2008

(65) Prior Publication Data

US 2009/0030034 A1 Jan. 29, 2009

Related U.S. Application Data

(63) Continuation of application No. 11/935,052, filed on Nov. 5, 2007, now abandoned, which is a continuation of application No. 11/684,792, filed on Mar. 12, 2007, now abandoned, which is a continuation of application No. 11/462,408, filed on Aug. 4, 2006, now abandoned, which is a continuation of application No. PCT/FR2005/000253, filed on Feb. 4, 2005.

(30) Foreign Application Priority Data

Feb. 5, 2004 (FR) .................................... 04 01094

(51) Int. Cl.
*A61K 31/44* (2006.01)
(52) U.S. Cl. ...................................................... 514/299
(58) Field of Classification Search .................. 514/299
See application file for complete search history.

(56) References Cited

U.S. PATENT DOCUMENTS 7,442,708 B2  10/2008  Badorc et al.

OTHER PUBLICATIONS

Ozaki, et al., Basic Fibroblast Growth Factor is Neither Necessary Nor Sufficient for the Development of retinal Neovascularization, Amer. J. of Pathology; Sep. 1998; vol. 153,No. 3; pp. 757-765.
Rousseau, et al., Involvement of Fibroblast Growth Factors in Choroidal Angiogenesis and retinal Vascularization, Experimental Eye Research; Aug. 2003; vol. 77,No. 2; pp. 147-156.
Rousseau, et al., Neural and Angiogenic Defects in Eyes of Transgenic Mice Expressing a Dominant-negative FGF Receptor in the Pigmented Cells, Experimental Eye Research; Oct. 2000; vol. 71,No. 4; pp. 395-404.
Soubrane, et al., Basic Fibroblast Growth factor Experimentally Induced Choroidal Angiogenesis in the Minipig, Current Eye Research; Mar. 1994; vol.13,No. 3; pp. 183-195.
Tobe, et al., Targeted Disruption of the FGF2 Gene Does Not Prevent Choroidal Neovascularization in a Murien Model., Amer. J. of Pathology; Nov. 1998; vol. 153,No. 5; pp. 1641-1646.
Yamada, et al., Cell Injury Unmasks a Latent Proangiogenic Phenotype in Mice With Increased Expression of FGF2 in the Retina, J. of Celluar Physiology; Oct. 2000; 185(1); pp. 135-142.

*Primary Examiner* — Raymond Henley, III
(74) *Attorney, Agent, or Firm* — Ronald G. Ort; James W. Bolcsak

(57) ABSTRACT

The present invention thus relates to the use of 1,2,3-substituted indolizine derivatives in the preparation of medicaments of use in the treatment of diseases related to pathological choroidal angiogenesis, which derivatives correspond to the following general formula (I):

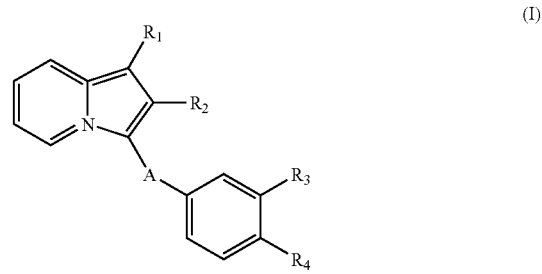

(I)

10 Claims, No Drawings

USE OF FGF INHIBITING SUBSTITUTED 1,2,3 INDOLIZINE DERIVATIVES IN THE PREPARATION OF MEDICAMENTS WHICH CAN BE USED TO TREAT DISEASES LINKED TO PATHOLOGICAL CHOROIDAL ANGIOGENESIS

Use of FGF-inhibiting 1,2,3-substituted indolizine derivatives in the preparation of medicaments which can be used to treat diseases linked to pathological choroidal angiogenesis.

It has been shown in vitro and in vivo that several growth factors participate in bringing about a "proangiogenesis" imbalance resulting in the uncontrolled proliferation of endothelial cells observed in neovascularization phenomena. FGF2 or bFGF (Fibroblast Growth Factor 2 or b) is the first and the best characterized. FGF2 is a protein of 18 000 D which induces the proliferation, the migration and the production of proteases by cultured endothelial cells and neovascularization in vivo. FGF2 interacts with endothelial cells via 2 classes of receptors, high-affinity tyrosine kinase receptors (FGFRs) and low affinity heparan sulphate proteoglycan receptors (HSPGs), situated at the surface of the cells and in the extracellular matrices. While the paracrine role of FGF2 with regard to endothelial cells is widely described, FGF2 might also be involved with regard to these cells through an autocrine process. Thus, FGF2 and its receptors represent highly relevant targets for therapies with the purpose of inhibiting angiogenesis processes (Keshet E, Ben-Sasson S A., *J. Clin. Invest.*, (1999), vol. 501, pp. 104-1497; Presta M, Rusnati M, Dell'Era P, Tanghetti E, Urbinati C, Giuliani R et al., *New York: Plenum Publishers*, (2000), pp. 7-34, Billottet C, Janji B, Thiery J. P., Jouanneau J, Oncogene, (2002), vol. 21, pp. 8128-8139).

A recent study has shown, via an experimental study model carried out on a mouse eye, the involvement of FGFs with regard to neovascularization (Rousseau et al., "Involvement of Fibroblasts Growth Factors in choroidal angiogenesis and retinal vascularization", Experimental Eye Research, Laboratoire des Mécanismes Moléculaires de l'angiogénèse [Angiogenesis Molecular Mechanisms Laboratory], INSERM EML01-13, Université de Bordeaux [Bordeaux University], France, 13 May 2003, pp. 147-156). The precise role of FGFs and of their receptors in pathological angiogenesis processes of the eye and in particular of the choroid remains, however, poorly known and leaves the way for sometimes differing hypotheses (Tobe et al., "Targeted disruption of the FGF2 gene does not prevent choroidal neovascularization in a murine model", Am. J. Pathol., 153, 1641-1646, 1998/Yamada et al., "Cell injury unmasks a latent proangiogenic phenotype in mice with increased expression of FGF2 in the retina, J. Cell Physiol., 185, 135-142, 2000).

International Patent Application WO 03/084956 discloses FGF-inhibiting derivatives of use, inter alia, in the treatment of pathologies in which angiogenesis appears to have a significant effect on the progression, such as, for example, chronic inflammatory diseases, such as rheumatoid arthritis or IBDs (Inflammatory Bowel Diseases). International Patent Application WO 03/084956 also discloses that such compounds are of use in the treatment of diseases due to vascular complications of diabetes, such as diabetic retinopathy, in which the blood vessels of the retina can become split or blocked.

It has now been found that some 1,2,3-substituted indolizine derivatives, which are antagonists of FGF receptors, referred to as FGFRs, are of use in the treatment of diseases related to pathological choroidal angiogenesis. Surprisingly, these compounds are as active when administered orally as locally, in particular intraocularly. The present invention thus relates to the use of 1,2,3-substituted indolizine derivatives in the preparation of medicaments of use in the treatment of diseases related to pathological choroidal angiogenesis, which derivatives correspond to the following general formula (I):

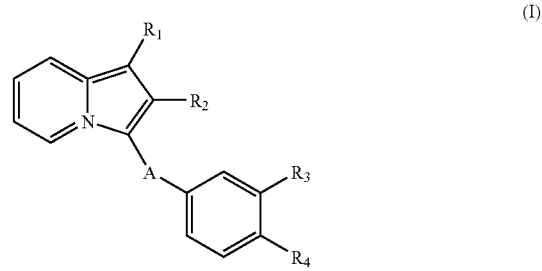

in which:

$R_1$ represents a hydroxyl radical, a linear or branched alkoxy radical of 1 to 5 carbon atoms, a carboxyl radical, an alkoxycarbonyl radical of 2 to 6 carbon atoms or a radical of formula:

—$NR_5R_6$

—NH—$SO_2$-Alk

—NH—$SO_2$-Ph

—NH—CO-Ph

—N(Alk)-CO-Ph

—NH—CO—NH-Ph

—NH—CO-Alk

—NH—$CO_2$-Alk

—O—$(CH_2)_n$-cAlk

—O-Alk-$COOR_7$

—O-Alk-O—$R_8$

—O-Alk-OH

—O-Alk-C($NH_2$):NOH

—O-Alk-$NR_5R_6$

—O-Alk-CN

—O—$(CH_2)_n$-Ph

—O-Alk-CO—$NR_5R_6$

—CO—NH—$(CH_2)_m$—$COOR_7$

—CO—NH-Alk in which

Alk represents an alkyl radical or an alkylene radical which is linear or branched and which has from 1 to 5 carbon atoms, cAlk represents a cycloalkyl radical of 3 to 6 carbon atoms, n represents an integer from 0 to 5, m represents an integer from 1 to 5, $R_5$ and $R_6$, which are identical or different, each represent a hydrogen atom, a linear or branched alkyl radical of 1 to 5 carbon atoms or a benzyl radical, $R_7$ represents a hydrogen atom or an alkyl radical of 1 to 5 carbon atoms, $R_8$ represents an alkyl radical of 1 to 5 carbon atoms or a —CO-Alk radical, Ph represents a phenyl radical optionally substituted by one or more halogen atoms, by one or more alkoxy radicals of 1 to 5 carbon atoms, by one or more carboxyl radicals or by one or more alkoxycarbonyl radicals of 2 to 6 carbon atoms, $R_2$ represents a hydrogen atom, an alkyl radical of 1 to 5 carbon atoms, an alkyl halide radical of 1 to 5 carbon atoms comprising 3 to 5 halogen atoms, a cycloalkyl radical of 3 to 6 carbon atoms or a phenyl radical optionally substituted by one or more halogen atoms, by one or more alkoxy radicals of 1 to 5 carbon atoms, by one or more carboxyl radicals or by one or more alkoxycarbonyl radicals of 2 to 6 carbon atoms, A represents a —CO—, —SO— or —SO$_2$— radical, $R_3$ and $R_4$, which are identical or different, each represent a hydrogen atom, an alkoxy radical of 1 to 5 carbon atoms, an amino radical, a carboxyl radical, an alkoxycarbonyl radical of 2 to 6 carbon atoms, a hydroxyl radical, a nitro radical, a hydroxyamino radical, a radical of formula -Alk-COOR$_7$

—NR$_5$R$_6$

—NH-Alk-COOR$_7$

—NH—COO-Alk

—N(R$_{11}$)—SO$_2$-Alk-NR$_9$R$_{10}$

—N(R$_{11}$)—SO$_2$-Alk

—N(R$_{11}$)-Alk-NR$_5$R$_6$

—N(R$_{11}$)—CO-Alk-NR$_9$R$_{10}$

—N(R$_{11}$)—CO-Alk

—N(R$_{11}$)—CO—CF$_3$

—NH-Alk-HetN

—O-Alk-NR$_9$R$_{10}$

—O-Alk-CO—NR$_5$R$_6$

—O-Alk-HetN in which n, m, Alk, $R_5$, $R_6$, and $R_7$ have the meaning given above for $R_1$; and $R_9$ and $R_{10}$, which are identical or different, each represent a hydrogen atom or an alkyl radical of 1 to 5 carbon atoms, $R_{11}$ represents a hydrogen atom or an -Alk-COOR$_{12}$ radical where $R_{12}$ represents a hydrogen atom, an alkyl radical of 1 to 5 carbon atoms or a benzyl radical, HetN represents a 5- or 6-membered heterocycle comprising at least one nitrogen atom and optionally one other heteroatom chosen from nitrogen and oxygen;

or else $R_3$ and $R_4$ together form an unsaturated 5- to 6-membered heterocycle, provided, however, that, when $R_3$ represents an alkoxy radical and $R_4$ represents an —O-Alk-NR$_9$R$_{10}$ radical or a hydroxyl radical, $R_1$ does not represent an alkoxy radical, optionally in the form of one of their pharmaceutically acceptable salts.

Preference is given to the use of the compounds of general formula (I) in which:

$R_1$ represents a hydroxyl radical, a linear or branched alkoxy radical of 1 to 5 carbon atoms, a carboxyl radical, an alkoxycarbonyl radical of 2 to 6 carbon atoms or a radical of formula:

—NR$_5$R$_6$

—NH—SO$_2$-Alk

—NH—SO$_2$-Ph

—NH—CO-Ph

—N(Alk)-CO-Ph

—NH—CO—NH-Ph

—NH—CO-Alk

—NH—CO$_2$-Alk

—O—(CH$_2$)$_n$-cAlk

—O-Alk-COOR$_7$

—O-Alk-O—R$_8$

—O-Alk-OH

—O-Alk-NR$_5$R$_6$

—O-Alk-CN

—O—(CH$_2$)$_n$-Ph

—O-Alk-CO—NR$_5$R$_6$

—CO—NH—(CH$_2$)$_m$—COOR$_7$

—CO—NH-Alk in which

Alk represents an alkyl radical or an alkylene radical which is linear or branched and which has from 1 to 5 carbon atoms, cAlk represents a cycloalkyl radical of 3 to 6 carbon atoms, n represents an integer from 0 to 5, m represents an integer from 1 to 5, $R_5$ and $R_6$, which are identical or different, each represent a hydrogen atom, a linear or branched alkyl radical of 1 to 5 carbon atoms or a benzyl radical, $R_7$ represents a hydrogen atom or an alkyl radical of 1 to 5 carbon atoms, $R_8$ represents an alkyl radical of 1 to 5 carbon atoms or a —CO-Alk radical, Ph represents a phenyl radical optionally substituted by one or more halogen atoms, by one or more alkoxy radicals of 1 to 5 carbon atoms, by one or more carboxyl radicals or by one or more alkoxycarbonyl radicals of 2 to 6 carbon atoms, $R_2$ represents an alkyl radical of 1 to 5 carbon atoms, a trifluoromethyl radical, a cycloalkyl radical of 3 to 6 carbon atoms or a phenyl radical optionally substituted by one or more halogen atoms, by one or more alkoxy radicals of 1 to 5 carbon atoms, by one or more carboxyl radicals or by one or more alkoxycarbonyl radicals of 2 to 6 carbon atoms, A represents a —CO— or —SO$_2$— radical, $R_3$ and $R_4$ which are identical or different, each represent a hydrogen atom, an alkoxy radical of 1 to 5 carbon atoms, an amino radical, a carboxyl radical, an alkoxycarbonyl radical of 2 to 6 carbon atoms, a nitro radical, a hydroxyamino radical, a radical of formula -Alk-COOR$_7$

—NR$_5$R$_6$

—NH-Alk-COOR$_7$

—NH—COO-Alk

—N(R$_{11}$)—SO$_2$-Alk-NR$_9$R$_{10}$

—N(R$_{11}$)—SO$_2$-Alk

—N(R$_{11}$)-Alk-NR$_5$R$_6$

—N(R$_{11}$)—CO-Alk-NR$_9$R$_{10}$

—N(R$_{11}$)—CO-Alk

—N(R$_{11}$)—CO—CF$_3$

—NH-Alk-HetN in which n, m, Alk, R$_5$, R$_6$ and R$_7$ have the meaning given above for R$_1$; and R$_9$ and R$_{10}$, which are identical or different, each represent a hydrogen atom or an alkyl radical of 1 to 5 carbon atoms, R$_{11}$ represents a hydrogen atom or an -Alk-COOR$_{12}$ radical where R$_{12}$ represents a hydrogen atom, an alkyl radical of 1 to 5 carbon atoms or a benzyl radical, HetN represents a 5- or 6-membered heterocycle comprising at least one nitrogen atom and optionally one other heteroatom chosen from nitrogen and oxygen, optionally in the form of one of their pharmaceutically acceptable salts.

The use of the compounds of general formula (I) in which:
R$_1$ represents an alkoxy radical of 1 to 5 carbon atoms, a carboxyl radical, an —O-Alk-COOH radical in which Alk represents a linear or branched alkylene radical of 1 to 5 carbon atoms, a radical of formula —O-Alk-Ph in which Alk represents an alkylene radical of 1 to 5 carbon atoms and Ph represents a phenyl radical optionally substituted by one or more halogen atoms or by one or more alkoxy radicals of 1 to 5 carbon atoms or by one or more carboxyl radicals, a radical of formula —NH—CO-Ph, a radical of formula —NH—SO$_2$-Ph or a radical of formula —NH—CO—NH-Ph, R$_2$ represents an alkyl radical of 1 to 5 carbon atoms, A represents a —CO— radical, R$_3$ and R$_4$, which are different, each represent a hydrogen atom, an alkoxy radical of 1 to 5 carbon atoms, an amino radical, a carboxyl radical or an alkoxycarbonyl radical of 2 to 6 carbon atoms, optionally in the form of one of their pharmaceutically acceptable salts, is particularly preferred.

Preference is more particularly given to the use of the compounds of formula (I) chosen from:
(4-amino-3-methoxyphenyl)(1-methoxy-2-methylindolizin-3-yl)methanone
3-(4-amino-3-methoxybenzoyl)-2-methylindolizin-1-ylcarboxylic acid
2-{[3-(4-amino-3-methoxybenzoyl)-2-methylindolizin-1-yl]oxy}acetic acid
(4-amino-3-methoxyphenyl){1-[(4-chlorobenzyl)oxy]-2-methylindolizin-3-yl}-methanone
(4-amino-3-methoxyphenyl){1-[(3-methoxybenzyl)oxy]-2-methylindolizin-3-yl}-methanone
4-({[3-(4-amino-3-methoxybenzoyl)-2-methylindolizin-1-yl]oxy}methyl)benzoic acid
3-(4-carboxybenzoyl)-2-methylindolizin-1-ylcarboxylic acid
methyl 3-[(1-methoxy-2-methylindolizin-3-yl)carbonyl]benzoate
4-[(1-methoxy-2-methylindolizin-3-yl)carbonyl]benzoic acid
2-amino-5-[(1-methoxy-2-methylindolizin-3-yl)carbonyl]benzoic acid
2-amino-5-({1-[(3-methoxybenzoyl)amino]-2-methylindolizin-3-yl}carbonyl)-benzoic acid
2-amino-5-({2-methyl-1-[(3,4,5-trimethoxybenzoyl)amino]indolizin-3-yl}carbonyl)benzoic acid
2-amino-5-({1-{[(3-methoxyphenyl)sulfonyl]amino}-2-methylindolizin-3-yl}-carbonyl)benzoic acid,
optionally in the form of one of their pharmaceutically acceptable salts.

Pathological choroidal angiogenesis is a process in which new capillary vessels of the choroid are generated. The choroid is a highly vascularized membrane of the eye: a complete network of fine capillaries providing for the nutrition of the iris and of the retina at the periphery of which it is found. Pathological choroidal angiogenesis is predominantly due to the occurrence of: a "proangiogenesis" imbalance but also to detrimental changes in the Bruch's membrane situated under the retina. Thus, the choroidal capillaries proliferate uncontrollably and, via a defect in the Bruch's membrane, invade the subretinal space (Lafaut et al., *Br. J. Ophtalmol.*, 84, 239-243).

Mention may be made, among the diseases related to pathological choroidal angiogenesis and in particular due to an anomaly in the Bruch's membrane, of age-related macular degeneration (AMD), severe myopia (Quaranta et al., *Graefe's Arch. Clin. Exp. Ophtalmol.*, 238, 101-103), pseudoxanthoma, presumed histoplasmosis syndrome, toxoplasmosis, sarcoidosis and Behcet's disease.

Thus, according to one of its aspects, the present invention relates to the use of 1,2,3-substituted indolizine derivatives of general formula (I) in the preparation of medicaments of use in the treatment of diseases related to pathological choroidal angiogenesis, such as age-related macular degeneration (AMD), severe myopia, pseudoxanthoma, presumed histoplasmosis syndrome, toxoplasmosis, sarcoidosis or Behcet's disease.

According to another of its aspects, a subject matter of the present invention is a pharmaceutical composition comprising at least one active principle corresponding to a compound of formula (I) or one of its pharmaceutically acceptable salts, optionally in combination with one or more inert and appropriate excipients, of use in the treatment of diseases related to pathological choroidal angiogenesis.

A subject matter of the present invention is in particular a pharmaceutical composition comprising at least one active principle corresponding to a compound of formula (I) chosen from:
(4-amino-3-methoxyphenyl)(1-methoxy-2-methylindolizin-3-yl)methanone
3-(4-amino-3-methoxybenzoyl)-2-methylindolizin-1-ylcarboxylic acid
2-{[3-(4-amino-3-methoxybenzoyl)-2-methylindolizin-1-yl]oxy}acetic acid
(4-amino-3-methoxyphenyl){1-[(4-chlorobenzyl)oxy]-2-methylindolizin-3-yl}-methanone
(4-amino-3-methoxyphenyl){1-[(3-methoxybenzyl)oxy]-2-methylindolizin-3-yl}-methanone
4-({[3-(4-amino-3-methoxybenzoyl)-2-methylindolizin-1-yl]oxy}methyl)benzoic acid 3-(4-carboxybenzoyl)-2-methylindolizin-1-ylcarboxylic acid methyl 3-[(1-methoxy-2-methylindolizin-3-yl)carbonyl]benzoate 4-[(1-methoxy-2-methylindolizin-3-yl)carbonyl]benzoic acid 2-amino-5-[(1-methoxy-2-methylindolizin-3-yl)carbonyl]benzoic acid 2-amino-5-({1-[(3-methoxybenzoyl)amino]-2-methylindolizin-3-yl}carbonyl)-benzoic acid 2-amino-5-({2-methyl-1-[(3,4,5-trimethoxybenzoyl)amino]indolizin-3-yl}carbonyl)benzoic acid 2-amino-5-({1-{[(3-methoxyphenyl)sulfonyl]amino}-2-methylindolizin-3-yl}-carbonyl)benzoic acid, optionally in combination with one or more inert and appropriate excipients.

Said excipients are chosen according to the pharmaceutical form and the method of administration desired: oral, intraocular or local.

The pharmaceutical compositions of the present invention are preferably administered orally or intraocularly.

Particularly preferably, the pharmaceutical compositions of the present invention are administered orally.

In the pharmaceutical compositions of the present invention for oral administration, the active principles can be administered in unit administration form, as a mixture with conventional pharmaceutical carriers. The appropriate unit administration forms comprise, for example, tablets, optionally scored, gelatin capsules, powders, granules and solutions or suspensions to be taken orally.

When a solid composition is prepared in the form of tablets, the main active ingredient is mixed with a pharmaceutical vehicle, such as gelatin, starch, lactose, magnesium stearate, talc, gum arabic or the like.

The tablets can be coated with sucrose or other appropriate materials or alternatively can be treated so that they have a prolonged or delayed activity and so that they continuously release a predetermined amount of active principle.

A preparation in the form of gelatin capsules is obtained by mixing the active ingredient with a diluent and by pouring the mixture obtained into soft or hard gelatin capsules.

A preparation in the syrup or elixir form can comprise the active ingredient in conjunction with a sweetener, preferably a calorie-free sweetener, methylparaben and propylparaben as antiseptics, and an appropriate colorant and flavoring.

The water-dispersible powders or granules can comprise the active ingredient as a mixture with dispersing agents, wetting agents or suspending agents, such as polyvinylpyrrolidone, and with sweeteners or flavor enhancers.

The active principle can also be formulated in the form of microcapsules, optionally with one or more carriers or additives.

In the pharmaceutical compositions according to the present invention, the active principle can also optionally be in the form of an inclusion complex in cyclodextrins, their ethers or their esters.

The pharmaceutical compositions for local administration can be in the form of various ophthalmic formulations. They can comprise in conjunction with the active principle, preservatives which are ophthalmologically acceptable, surfactants, viscosity agents, agents which promote the penetration of the active principle, buffers, sodium chloride and water, in order to obtain sterile solutions or suspensions for ophthalmological use.

The ophthalmic solutions can be prepared by dissolving the active principles in isotonic buffer solutions. These solutions can comprise surfactants in order to facilitate the dissolution of the active principle. In order to allow better application, the ophthalmic solutions can also comprise a thickening agent, such as hydroxymethylcellulose, hydroxyethylcellulose, hydroxypropylmethylcellulose or polyvinylpyrrolidone.

In order to prepare sterile ophthalmic ointments, the active principle is combined with a preservative in an appropriate vehicle, for example liquid lanolin. Sterile gels can be prepared by suspending the active principle in a hydrophilic base comprising carbopol 940 or other analogous compounds.

For local application, the pharmaceutical compositions according to the invention are preferable in the form of solutions or suspensions having a pH of 4 to 8. The concentration of the active principle should be from 0.0001% to 5% w/w, preferably 0.0001 to 1%. Depending on the doctor's instructions, one to two drops of these compositions can be administered 1 to 4 times daily.

The amount of active principle to be administered depends, as always, on the degree of progression of the disease and on the age and weight of the patient.

In particular, the pharmaceutical compositions which can be administered orally according to the invention comprise recommended doses of active principle of between 1 and 900 mg/kg/day.

Preferably, the pharmaceutical compositions which can be administered orally according to the invention comprise recommended doses of active principle of between 3 and 300 mg/kg/day.

Particularly preferably, the pharmaceutical compositions which can be administered orally according to the invention comprise recommended doses of active principle of between 1 and 100 mg/kg/day.

The following example, given without implied limitation, illustrates the present invention.

EXAMPLE

Laser Induction of Choroidal Neovascularization

1. Equipment and Method

C57B16 mice were used in these experiments. A model of laser-induced choroidal neovascularization (4 impacts per eye around the papilla) was applied to the animals as described by Tobe et al. Am. J. Pathol., 1998).

On day 14 after the induction and after monitoring by angiography, which makes it possible to estimate the percentage of lesions developing neovascularization, the animals are sacrificed and the eyeballs are enucleated for histological analysis. The mice are treated orally with one of the compounds of formula (I) during the last 7 days. The dose chosen for the monohydrate of the sodium salt of 2-amino-5-[(1-methoxy-2-methylindolizin-3-yl)carbonyl]benzoic acid is 30 mg/kg/day. The vehicle used is a 0.6% solution of methylcellulose in water.

Four mice are used for the control group and six mice for the treated group.

The size of the neovascular reaction is estimated from frozen sections by morphometric evaluations of the thickness using a computerized image analysis system. These sections are either simply colored with hematoxylin or examined in immunofluorescence using an antibody which makes it possible to localize the vascular structures (anti-CD31).

Estimation is carried out by measuring the B/C ratio between, on the one hand, the EPR and the peak of the neovascular reaction ("B"), and, on the other hand, the thickness of the adjacent intact choroidal layer ("C"). This quantifying system was preferred to measuring surface areas of lesions as it is independent of the orientation of the histological sections.

2. Results

The angiographies carried out on day 14 showed the induction of neovessels in 72% of the lesions created by the laser in the control mice.

The histological analysis and the immunohistochemistry carried out using the antibody anti-CD31 confirmed the presence of neoformed capillaries in the areas showing an important diffusion of fluorescein in the angiography in the control group. In contrast, animals treated with the compound exhibited only a moderate thickening of the choriocapillary where the impacts occurred, without obvious sign of neovascularization.

The quantifying of the laser-induced reaction carried out by measuring the B/C ratio showed a significant reduction of the order of 50% in the reaction ($p<0.001$) in the mice treated with the compound in comparison with the control mice.

These results confirm the great advantage of the use of compounds of formula (I) in the preparation of medicaments of use in the treatment of diseases related to pathological choroidal angiogenesis.

What is claimed is:

1. A method for the treatment of a disease related to pathological choroidal angiogenesis, the method comprising administering to a patient in need thereof a pharmaceutically effective dose of a 1,2,3-substituted indolizine derivative compound of the following general formula (I):

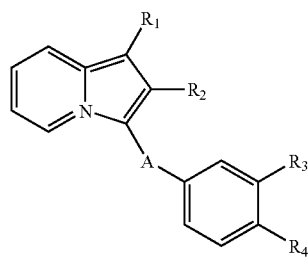

(I)

in which:
$R_1$ represents a hydroxyl radical, a linear or branched alkoxy radical of 1 to 5 carbon atoms, a carboxyl radical, an alkoxycarbonyl radical of 2 to 6 carbon atoms or a radical of formula:

—$NR_5R_6$

—NH—$SO_2$-Alk

—NH—$SO_2$-Ph

—NH—CO-Ph

—N(Alk)-CO-Ph

—NH—CO—NH-Ph

—NH—CO-Alk

—NH—$CO_2$-Alk

—O—$(CH_2)_n$-cAlk

—O-Alk-$COOR_7$

—O-Alk-O—$R_8$

—O-Alk-OH

—O-Alk-C($NH_2$):NOH

—O-Alk-$NR_5R_6$

—O-Alk-CN

—O—$(CH_2)_n$-Ph

—O-Alk-CO—$NR_5R_6$

—CO—NH—$(CH_2)_m$—$COOR_7$

—CO—NH-Alk in which
Alk represents an alkyl radical or an alkylene radical which is linear or branched and which has from 1 to 5 carbon atoms,
cAlk represents a cycloalkyl radical of 3 to 6 carbon atoms,
n represents an integer from 0 to 5,
m represents an integer from 1 to 5,
$R_5$ and $R_6$, which are identical or different, each represent a hydrogen atom, a linear or branched alkyl radical of 1 to 5 carbon atoms or a benzyl radical,
$R_7$ represents a hydrogen atom or an alkyl radical of 1 to 5 carbon atoms,
$R_8$ represents an alkyl radical of 1 to 5 carbon atoms or a —CO-Alk radical,
Ph represents a phenyl radical optionally substituted by one or more halogen atoms, by one or more alkoxy radicals of 1 to 5 carbon atoms, by one or more carboxyl radicals or by one or more alkoxycarbonyl radicals of 2 to 6 carbon atoms,
$R_2$ represents a hydrogen atom, an alkyl radical of 1 to 5 carbon atoms, an alkyl halide radical of 1 to 5 carbon atoms comprising 3 to 5 halogen atoms, a cycloalkyl radical of 3 to 6 carbon atoms or a phenyl radical optionally substituted by one or more halogen atoms, by one or more alkoxy radicals of 1 to 5 carbon atoms, by one or more carboxyl radicals or by one or more alkoxycarbonyl radicals of 2 to 6 carbon atoms,
A represents a —CO—, —SO— or —$SO_2$— radical,
$R_3$ and $R_4$, which are identical or different, each represent a hydrogen atom, an alkoxy radical of 1 to 5 carbon atoms, an amino radical, a carboxyl radical, an alkoxycarbonyl radical of 2 to 6 carbon atoms, a hydroxyl radical, a nitro radical, a hydroxyamino radical, a radical of formula -Alk-$COOR_7$

—$NR_5R_6$

—NH-Alk-$COOR_7$

—NH—COO-Alk

—N($R_{11}$)—$SO_2$-Alk-$NR_9R_{10}$

—N($R_{11}$)—$SO_2$-Alk

—N($R_{11}$)-Alk-$NR_5R_6$

—N($R_{11}$)—CO-Alk-$NR_9R_{10}$

—N($R_{11}$)—CO-Alk

—N($R_{11}$)—CO—$CF_3$

—NH-Alk-HetN

—O-Alk-NR$_9$R$_{10}$

—O-Alk-CO—NR$_5$R$_6$

—O-Alk-HetN in which n, m, Alk, R$_5$, R$_6$ and R$_7$ have the meaning given above for R$_1$; and R$_9$ and R$_{10}$, which are identical or different, each represent a hydrogen atom or an alkyl radical of 1 to 5 carbon atoms, R$_{11}$ represents a hydrogen atom or an -Alk-COOR$_{12}$ radical where R$_{12}$ represents a hydrogen atom, an alkyl radical of 1 to 5 carbon atoms or a benzyl radical, HetN represents a 5- or 6-membered heterocycle comprising at least one nitrogen atom and optionally one other heteroatom chosen from nitrogen and oxygen;

or else R$_3$ and R$_4$ together form an unsaturated 5- to 6-membered heterocycle, provided, however, that when R$_3$ represents an alkoxy radical and R$_4$ represents an —O-Alk-NR$_9$R$_{10}$ radical or a hydroxyl radical, R$_1$ does not represent an alkoxy radical, or a pharmaceutically acceptable salt thereof.

2. The method of claim 1, wherein in the compound of general formula (I):

R$_1$ represents a hydroxyl radical, a linear or branched alkoxy radical of 1 to 5 carbon atoms, a carboxyl radical, an alkoxycarbonyl radical of 2 to 6 carbon atoms or a radical of formula:

—NR$_5$R$_6$

—NH—SO$_2$-Alk

—NH—SO$_2$-Ph

—NH—CO-Ph

—N(Alk)-CO-Ph

—NH—CO—NH-Ph

—NH—CO-Alk

—NH—CO$_2$-Alk

—O—(CH$_2$)$_n$-cAlk

—O-Alk-COOR$_7$

—O-Alk-O—R$_8$

—O-Alk-OH

—O-Alk-NR$_5$R$_6$

—O-Alk-CN

—O—(CH$_2$)$_n$-Ph

—O-Alk-CO—NR$_5$R$_6$

—CO—NH—(CH$_2$)$_m$—COOR$^7$

—CO—NH-Alk in which

Alk represents an alkyl radical or an alkylene radical which is linear or branched and which has from 1 to 5 carbon atoms, cAlk represents a cycloalkyl radical of 3 to 6 carbon atoms, n represents an integer from 0 to 5, m represents an integer from 1 to 5, R$_5$ and R$_6$, which are identical or different, each represent a hydrogen atom, a linear or branched alkyl radical of 1 to 5 carbon atoms or a benzyl radical, R$_7$ represents a hydrogen atom or an alkyl radical of 1 to 5 carbon atoms, R$_8$ represents an alkyl radical of 1 to 5 carbon atoms or a —CO-Alk radical, Ph represents a phenyl radical optionally substituted by one or more halogen atoms, by one or more alkoxy radicals of 1 to 5 carbon atoms, by one or more carboxyl radicals or by one or more alkoxycarbonyl radicals of 2 to 6 carbon atoms, R$_2$ represents an alkyl radical of 1 to 5 carbon atoms, a trifluoromethyl radical, a cycloalkyl radical of 3 to 6 carbon atoms or a phenyl radical optionally substituted by one or more halogen atoms, by one or more alkoxy radicals of 1 to 5 carbon atoms, by one or more carboxyl radicals or by one or more alkoxycarbonyl radicals of 2 to 6 carbon atoms, A represents a —CO— or —SO$_2$— radical, R$_3$ and R$_4$, which are identical or different, each represent a hydrogen atom, an alkoxy radical of 1 to 5 carbon atoms, an amino radical, a carboxyl radical, an alkoxycarbonyl radical of 2 to 6 carbon atoms, a nitro radical, a hydroxyamino radical, a radical of formula -Alk-COOR$_7$

—NR$_5$R$_6$

—NH-Alk-COOR$_7$

—NH—COO-Alk

—N(R$_{11}$)—SO$_2$-Alk-NR$_9$R$_{10}$

—N(R$_{11}$)—SO$_2$-Alk

—N(R$_{11}$)-Alk-NR$_5$R$_6$

—N(R$_{11}$)—CO-Alk-NR$_9$R$_{10}$

—N(R$_{11}$)—CO-Alk

—N(R$_{11}$)—CO—CF$_3$

—NH-Alk-HetN in which n, m, Alk, R$_5$, R$_6$ and R$_7$ have the meaning given above for R$_1$; and R$_9$ and R$_{10}$, which are identical or different, each represent a hydrogen atom or an alkyl radical of 1 to 5 carbon atoms, R$_{11}$ represents a hydrogen atom or an -Alk-COOR$_{12}$ radical where R$_{12}$ represents a hydrogen atom, an alkyl radical of 1 to 5 carbon atoms or a benzyl radical, HetN represents a 5- or 6-membered heterocycle comprising at least one nitrogen atom and optionally one other heteroatom chosen from nitrogen and oxygen, or a pharmaceutically acceptable salt thereof.

3. The method of claim 1, wherein in the compound of general formula (I):

R$_1$ represents an alkoxy radical of 1 to 5 carbon atoms, a carboxyl radical, an —O-Alk-COOH radical in which Alk represents a linear or branched alkylene radical of 1 to 5 carbon atoms, a radical of formula —O-Alk-Ph in which Alk represents an alkylene radical of 1 to 5 carbon atoms and Ph represents a phenyl radical optionally substituted by one or more halogen atoms or by one or more alkoxy radicals of 1 to 5 carbon atoms or by one or more carboxyl radicals, a radical of formula —NH—CO-Ph, a radical of formula —NH—SO$_2$-Ph or a radical of formula —NH—CO—NH-Ph, $R_2$ represents an alkyl radical of 1 to 5 carbon atoms, A represents a —CO— radical, $R_3$ and $R_4$, which are different, each represent a hydrogen atom, an alkoxy radical of 1 to 5 carbon atoms, an amino radical, a carboxyl radical or an alkoxycarbonyl radical of 2 to 6 carbon atoms, or a pharmaceutically acceptable salt thereof.

4. The method of claim 1, wherein the compound of general formula (I) is chosen from:
- (4-amino-3-methoxyphenyl)(1-methoxy-2-methylindolizin-3-yl)methanone,
- 3-(4-amino-3-methoxybenzoyl)-2-methylindolizin-1-yl-carboxylic acid,
- 2-{[3-(4-amino-3-methoxybenzoyl)-2-methylindolizin-1-yl]oxy}acetic acid,
- (4-amino-3-methoxyphenyl){1-[(4-chlorobenzyl)oxy]-2-methylindolizin-3-yl}-methanone,
- (4-amino-3-methoxyphenyl){1-[(3-methoxybenzyl)oxy]-2-methylindolizin-3-yl}-methanone,
- 4-({[3-(4-amino-3-methoxybenzoyl)-2-methylindolizin-1-yl]oxy}methyl)benzoic acid,
- 3-(4-carboxybenzoyl)-2-methylindolizin-1-ylcarboxylic acid,
- methyl 3-[(1-methoxy-2-methylindolizin-3-yl)carbonyl]benzoate,
- 4-[(1-methoxy-2-methylindolizin-3-yl)carbonyl]benzoic acid,
- 2-amino-5-[(1-methoxy-2-methylindolizin-3-yl)carbonyl]benzoic acid,
- 2-amino-5-({1-[(3-methoxybenzoyl)amino]-2-methylindolizin-3-yl}carbonyl)benzoic acid,
- 2-amino-5-({2-methyl-1-[(3,4,5-trimethoxybenzoyl)amino]indolizin-3-yl}carbonyl)benzoic acid,
- 2-amino-5-({1-{[(3-methoxyphenyl)sulfonyl]amino}-2-methylindolizin-3-yl}-carbonyl)benzoic acid,
or a pharmaceutically acceptable salt thereof.

5. The method of claim 1, wherein the disease related to pathological choroidal angiogenesis is chosen from age-related macular degeneration (AMD), severe myopia, pseudoxanthoma, presumed histoplasmosis syndrome, toxoplasmosis, sarcoidosis or Behcet's disease.

6. The method of claim 1, wherein the compound is administered orally, intraocularly or locally.

7. The method of claim 6 wherein the compound is administered orally and the dose is between 1 and 900 mg/kg/day.

8. The method of claim 7, wherein the dose is between 3 and 300 mg/kg/day.

9. The method of claim 7, wherein the dose is between 1 and 100 mg/kg/day.

10. The method of claim 7, wherein the compound is in the form of a pharmaceutically active salt.

\* \* \* \* \*

UNITED STATES PATENT AND TRADEMARK OFFICE
CERTIFICATE OF CORRECTION

PATENT NO. : 8,034,828 B2
APPLICATION NO. : 12/201075
DATED : October 11, 2011
INVENTOR(S) : Alain Badorc et al.

It is certified that error appears in the above-identified patent and that said Letters Patent is hereby corrected as shown below:

On the first page, item (54), in column 1, line 1-2, delete "FGF INHIBITING SUBSTITUTED 1,2,3" and insert -- FGF-INHIBITING 1,2,3-SUBSTITUTED --, therefor.

On the first page, item (57), in column 2, line 6, delete " 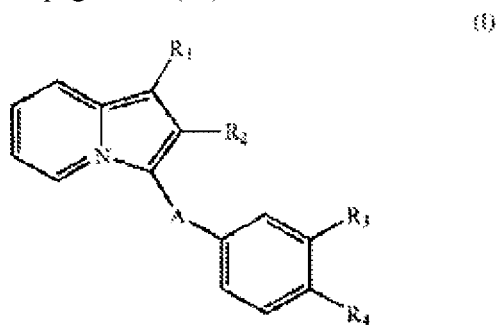 " and insert -- 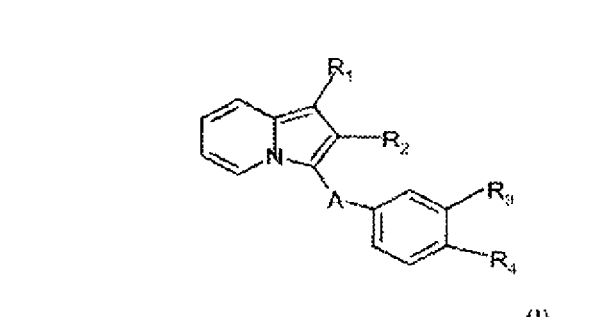 --, therefor.

In column 1, line 1-2, delete "FGF INHIBITING SUBSTITUTED 1,2,3" and insert -- FGF-INHIBITING 1,2,3-SUBSTITUTED --, therefor.

In column 2, line 10-20, delete " 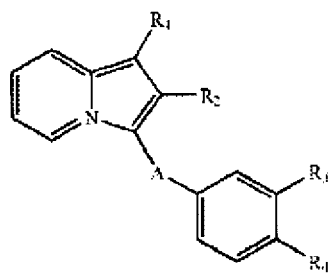 " and insert

Signed and Sealed this
Twentieth Day of March, 2012

David J. Kappos
*Director of the United States Patent and Trademark Office*

CERTIFICATE OF CORRECTION (continued)
U.S. Pat. No. 8,034,828 B2

-- 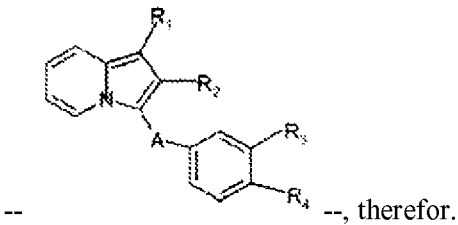 --, therefor.

In column 9, line 30-40, in claim 1, delete " 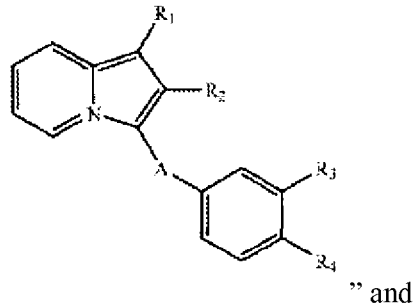 " and insert -- 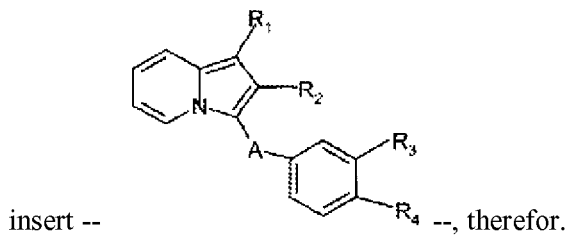 --, therefor.

In column 11, line 61, In Claim 2, delete "—CO—NH—(CH$_2$)$_m$—COOR$^7$" and insert -- —CO—NH—(CH$_2$)$_m$—COOR$_7$ --, therefor.